United States Patent
Yang

(10) Patent No.: US 11,141,344 B2
(45) Date of Patent: Oct. 12, 2021

(54) ASSISTANT APPARATUS FOR DEGENERATIVE JOINT

(71) Applicant: Chin-Sung Yang, Taipei (TW)

(72) Inventor: Chin-Sung Yang, Taipei (TW)

(*) Notice: Subject to any disclaimer, the term of this patent is extended or adjusted under 35 U.S.C. 154(b) by 341 days.

(21) Appl. No.: 16/233,108

(22) Filed: Dec. 27, 2018

(65) Prior Publication Data
US 2020/0206065 A1 Jul. 2, 2020

(51) Int. Cl.
*A61H 1/02* (2006.01)
*A61H 3/00* (2006.01)
*A61F 5/00* (2006.01)
*A61H 3/02* (2006.01)
*A61F 5/01* (2006.01)

(52) U.S. Cl.
CPC .......... *A61H 3/02* (2013.01); *A61F 5/0123* (2013.01); *A61H 1/0262* (2013.01); *A61H 3/0277* (2013.01); *A61H 2003/005* (2013.01); *A61H 2003/0283* (2013.01); *A61H 2201/164* (2013.01); *A61H 2201/1635* (2013.01)

(58) Field of Classification Search
CPC ............... A61H 3/02; A61H 1/0262; A61H 2201/1635; A61H 2003/005; A61H 2201/164; A61H 3/00; A61H 2201/1642; A61H 2205/10; A61H 1/0237; A61H 2003/007; A61H 2201/1284; A61H 2201/0192; A61H 2201/165; A61F 5/0123
See application file for complete search history.

(56) References Cited

U.S. PATENT DOCUMENTS

| | | | |
|---|---|---|---|
| 2,267,848 A | | 12/1941 | Taylor |
| 5,671,765 A | * | 9/1997 | Hagberg, Jr. ............ A61H 3/02 135/68 |
| 9,375,377 B1 | * | 6/2016 | Edwards ............... A61F 5/0123 |
| 9,861,501 B2 | | 1/2018 | Yoon et al. |
| 2007/0004570 A1 | | 1/2007 | Afanasenko |
| 2008/0039756 A1 | * | 2/2008 | Thorsteinsson ...... A61B 5/4585 602/23 |
| 2009/0114257 A1 | * | 5/2009 | Sutton ..................... A61H 3/02 135/72 |

(Continued)

FOREIGN PATENT DOCUMENTS

| | | |
|---|---|---|
| CN | 202243769 U | 5/2012 |
| CN | 204147143 U | 2/2015 |

(Continued)

*Primary Examiner* — Quang D Thanh
(74) *Attorney, Agent, or Firm* — Li & Cai Intellectual Property Office

(57) ABSTRACT

An assistant apparatus for degenerative joint includes an apparatus main body, a first leg-lifting mechanism, and a second leg-lifting mechanism. The apparatus main body has an upper section, a middle section, and a lower section. The middle section is connected between the upper section and the lower section. The upper end of the upper section is provided with a supporting member. The lower end of the lower section is provided with a carrying member. The upper section is bendable relative to the middle section, and the middle section is bendable relative to the lower section. The upper section, the middle section, the lower section, the first leg-lifting mechanism, and the second leg-lifting mechanism each include an elastic buffering mechanism for providing elastic buffering effects.

3 Claims, 9 Drawing Sheets

(56) References Cited

U.S. PATENT DOCUMENTS

| | | | |
|---|---|---|---|
| 2015/0209213 A1 | 7/2015 | Kline | |
| 2016/0317340 A1* | 11/2016 | Jangir | ................. A41F 9/00 |
| 2016/0331624 A1* | 11/2016 | Sankai | ................. B25J 9/101 |
| 2017/0027735 A1* | 2/2017 | Walsh | ................. A61F 5/0102 |

FOREIGN PATENT DOCUMENTS

| | | |
|---|---|---|
| CN | 103610568 B | 5/2015 |
| CN | 104635732 A | 5/2015 |
| CN | 105310866 A | 2/2016 |
| CN | 106420278 A | 2/2017 |
| CN | 105213155 B | 3/2017 |
| CN | 205988396 U | 3/2017 |
| CN | 106821684 A | 6/2017 |
| CN | 107510575 A | 12/2017 |
| EP | 2959869 A1 | 12/2015 |
| JP | 2509800 B2 | 6/1996 |
| KR | 1020160120835 A | 10/2016 |
| TW | M574911 U | 3/2019 |
| WO | WO2015148576 A1 | 10/2015 |

\* cited by examiner

ASSISTANT APPARATUS FOR DEGENERATIVE JOINT

FIELD OF THE DISCLOSURE

The present disclosure relates to an assistant apparatus, and more particularly to an assistant apparatus that helps elderly people suffering from the degenerative joint disease to walk.

BACKGROUND OF THE DISCLOSURE

In an era of aging society, degenerative joint disease is a very common issue for elderly people. Whenever the weather changes drastically or the temperature drops suddenly, they tend to suffer from joint swelling, inflammation and severe pain, which make it difficult for them to walk. This has led to significant restrictions to their mobility and activity, and in certain cases, artificial joints may need to be implanted in elderlies suffering from more severe joint conditions. While conventional assistant apparatuses such as crutches can aid with walking, they cannot effectively reduce the weight of the human body borne by the joints, so that their effects are rather limited.

SUMMARY OF THE DISCLOSURE

In response to the above-referenced technical inadequacies, the present disclosure provides an assistant apparatus that can effectively share the weight of the human body to reduce the burden on the joints, thereby helping the user in walking and effectively reducing the discomfort of the waist and the joints.

In one aspect, the present disclosure provides an assistant apparatus for degenerative joint, including an apparatus main body, a first leg-lifting mechanism, and a second leg-lifting mechanism. The apparatus main body has an upper section, a middle section, and a lower section. The middle section is connected between the upper section and the lower section. The upper end of the upper section is provided with a supporting member. The lower end of the lower section is provided with a carrying member. The upper section is bendable relative to the middle section, and the middle section is bendable relative to the lower section. The first leg-lifting mechanism is connected between the upper section and the middle section of the apparatus main body. The second leg-lifting mechanism is connected between the middle section and the middle section of the apparatus main body. The upper section, the middle section, the lower section, the first leg-lifting mechanism, and the second leg-lifting mechanism of the apparatus main body each include an elastic buffering mechanism to provide elastic buffer effects.

Therefore, the assistant apparatus of the present disclosure is a kind of walking crutch that can support the weight of the human body in a multi-sectional manner and generate elastic buffering effect. It can also use the weight of the human body to store kinetic energy when it is stepped down on, so as to help users save energy when they lift their thighs and calves. The assistant apparatus of the present disclosure can effectively reduce the discomfort of the waist and the joints, and is suitable for patients with symptoms such as deteriorative joints, osteoporosis, mild stroke, as well as for traffic accident rehabilitation so that patients can walk more effortlessly and easily. Furthermore, the elastic buffering mechanism of the assistant apparatus of the present disclosure has an adjustment function, with which the elastic force can be appropriately adjusted according to the heights of the users and the use conditions.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The present disclosure will become more fully understood from the following detailed description and accompanying drawings.

DETAILED DESCRIPTION OF THE EXEMPLARY EMBODIMENTS

Figure 1:
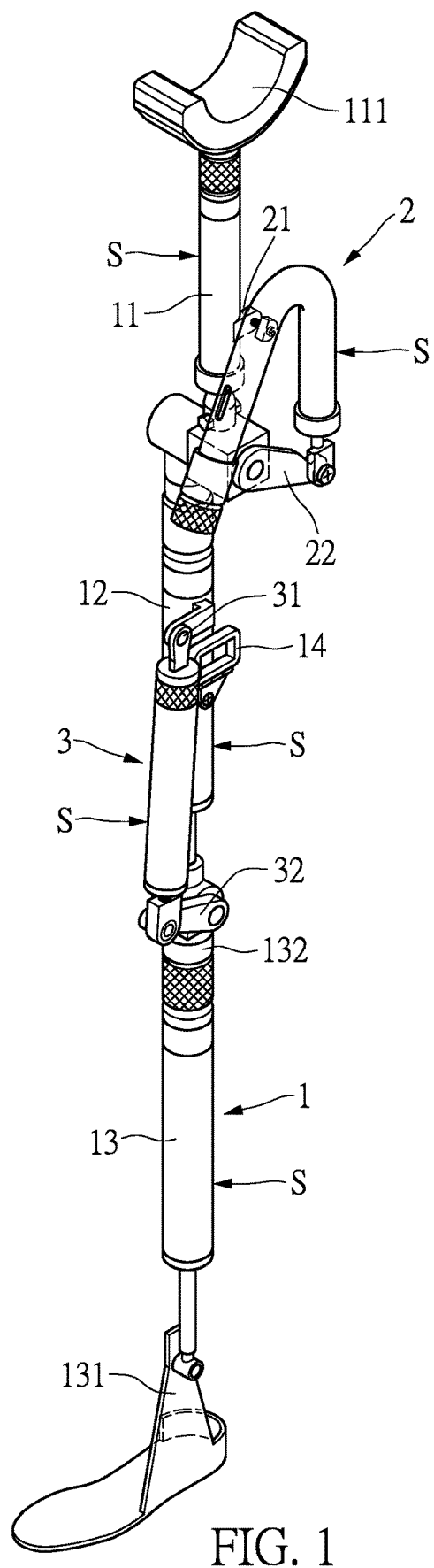
FIG. 1 is a perspective view of an assistant apparatus for degenerative joint of the present disclosure.
Figure 2:
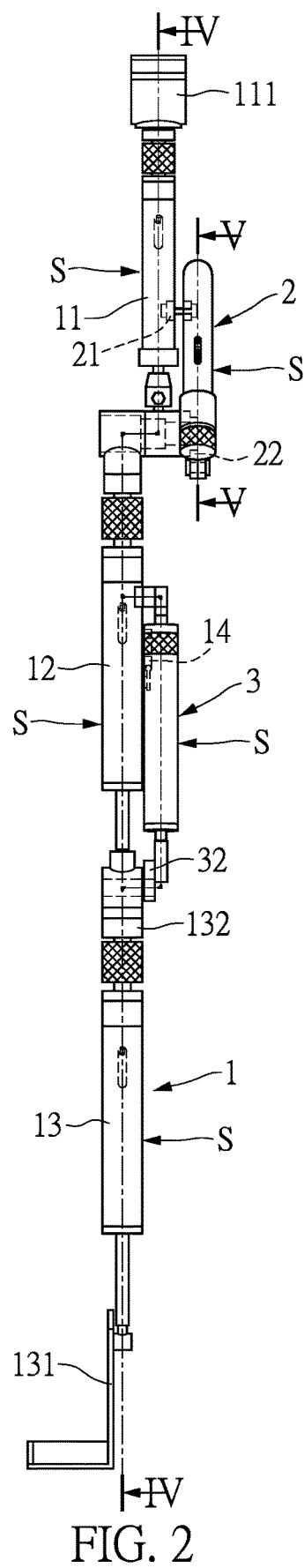
FIG. 2 is a front view of the assistant apparatus for degenerative joint of the present disclosure.
Figure 3:
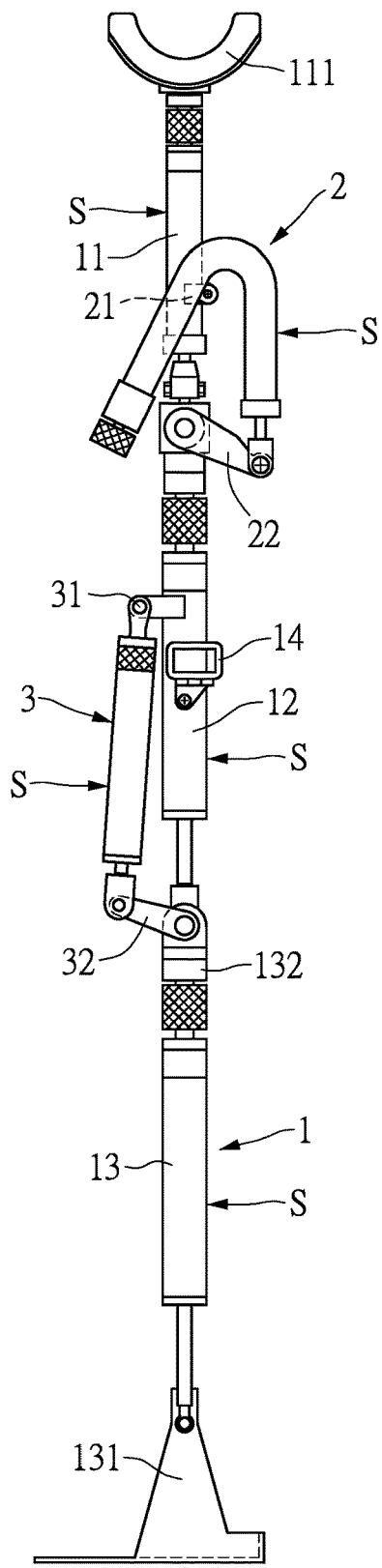
FIG. 3 is a side view of the assistant apparatus for degenerative joint of the present disclosure.
Figure 4:
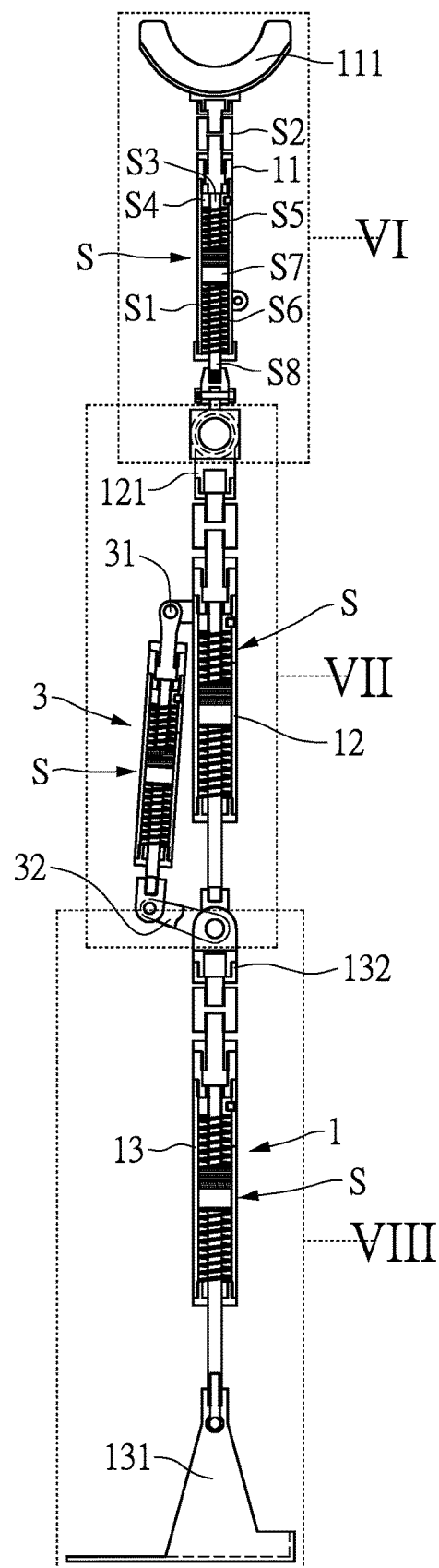
FIG. 4 is a cross-sectional view taken along line IV-IV of FIG. 2.
Figure 5:
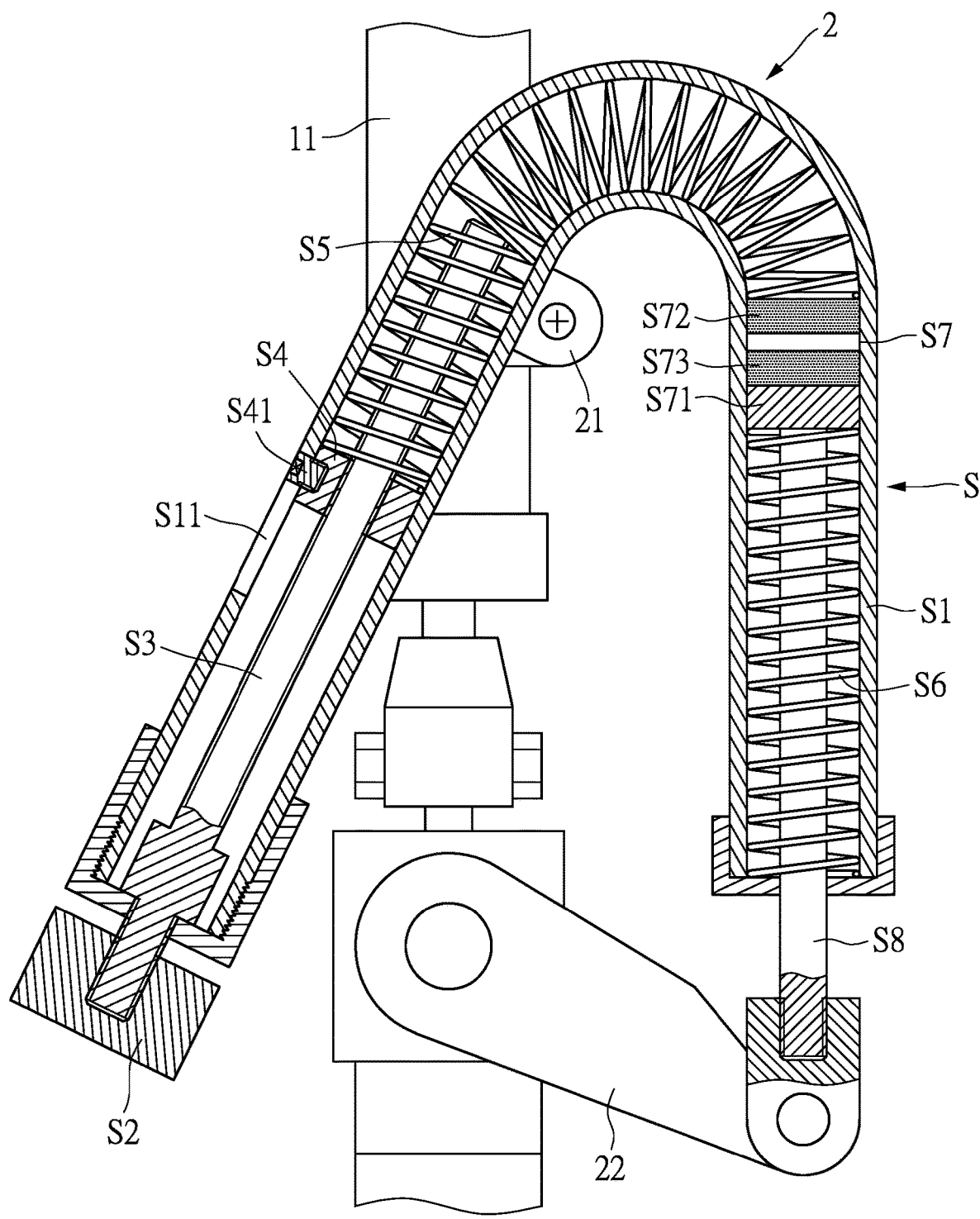
FIG. 5 is a cross-sectional view taken along line V-V of FIG. 2.
Figure 6:
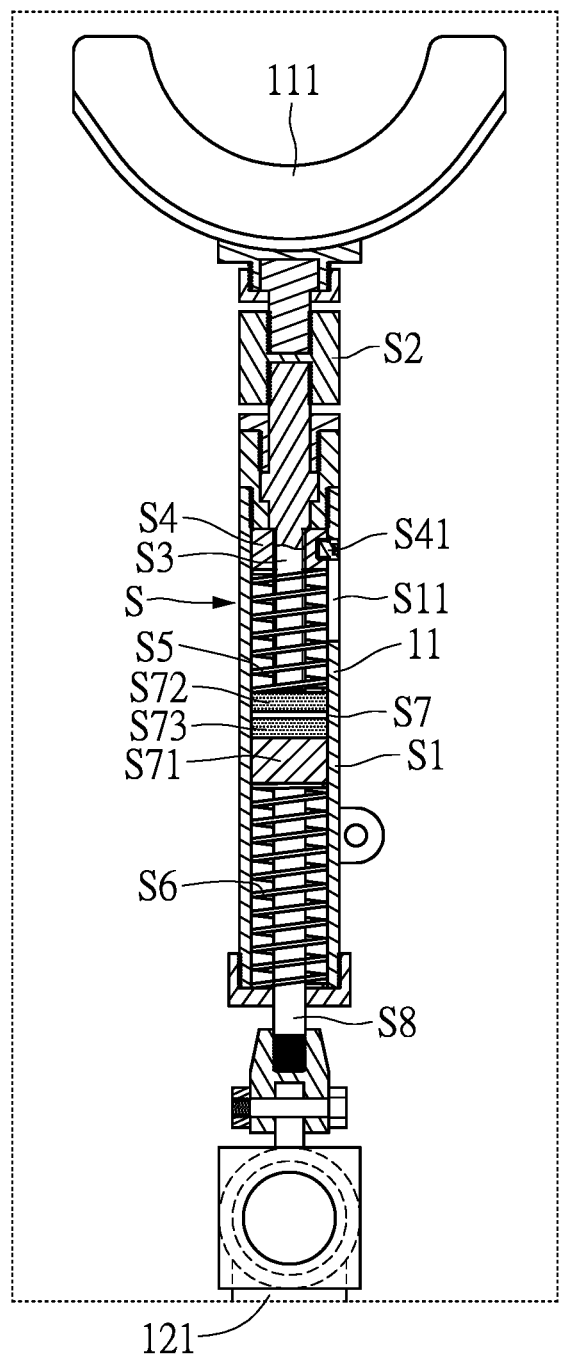
FIG. 6 is a detailed view of section VI of FIG. 4.
Figure 7:
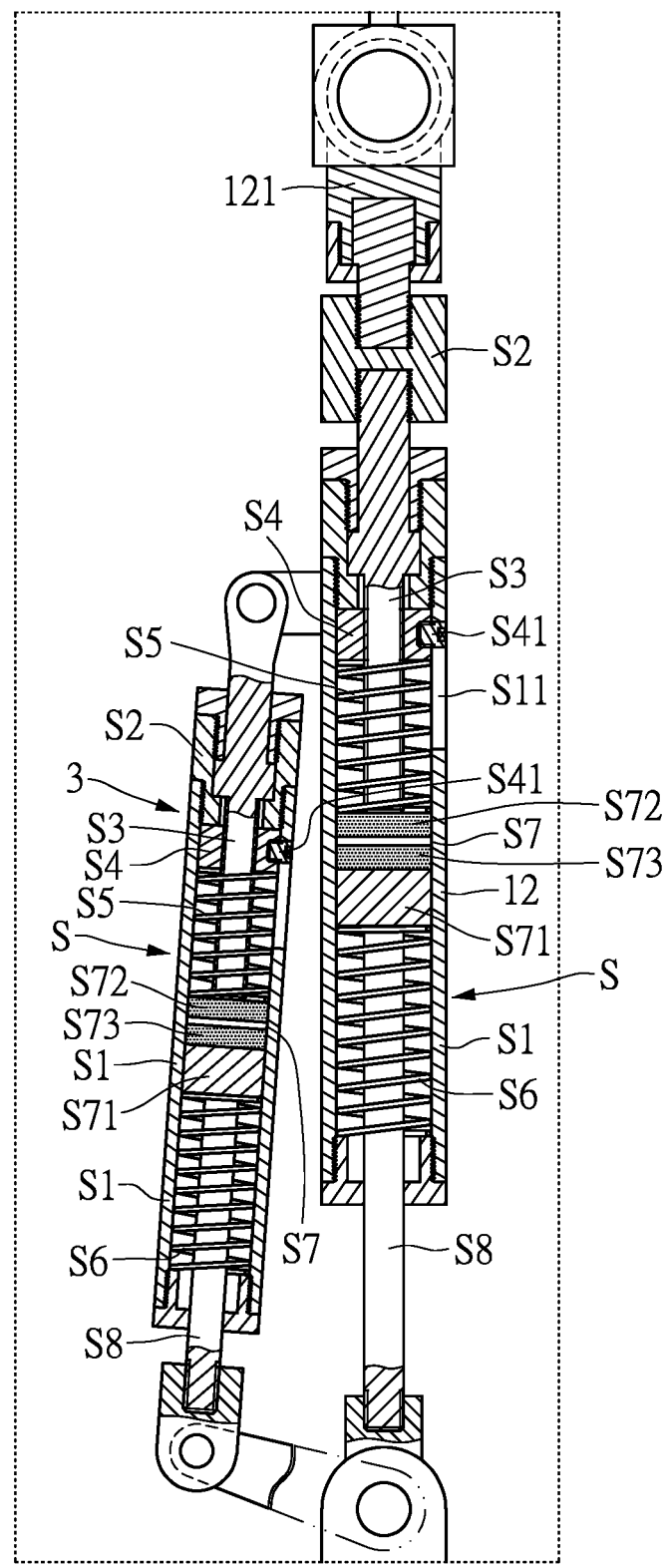
FIG. 7 is a detailed view of section VII of FIG. 4.
Figure 8:
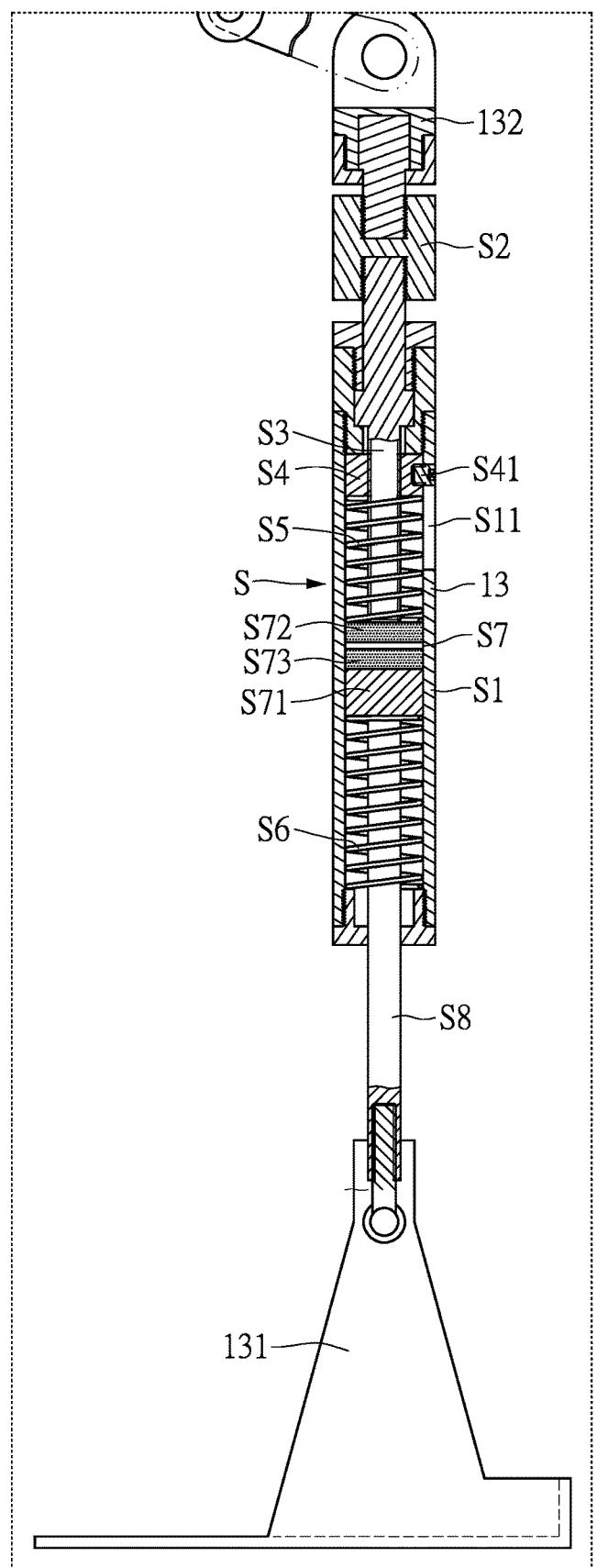
FIG. 8 is a detailed view of section VIII of FIG. 4.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

Referring to FIG. 1 to FIG. 4, the assistant apparatus for degenerative joint in accordance with the present disclosure includes an apparatus main body 1, a first leg-lifting mechanism 2, and a second leg-lifting mechanism 3. The apparatus main body 1 has an upper section 11, a middle section 12, and a lower section 13. The upper section 11, the middle section 12, and the lower section 13 are sequentially arranged from top to bottom, and the middle section 12 is connected between the upper section 11 and the lower section 13. The upper end of the middle section 12 can for example be pivotally connected to the lower end of upper section 11 such that the upper section 11 is bendable relative to the middle section 12, and the middle section 12 can swing back and forth using its upper end as the fulcrum. The lower end of middle section 12 can for example be pivotally connected to the upper end of the lower section 13 such that middle section 12 is bendable relative to the lower section 13, and the lower section 13 can swing back and forth using its upper end as the fulcrum.

Figure 10:
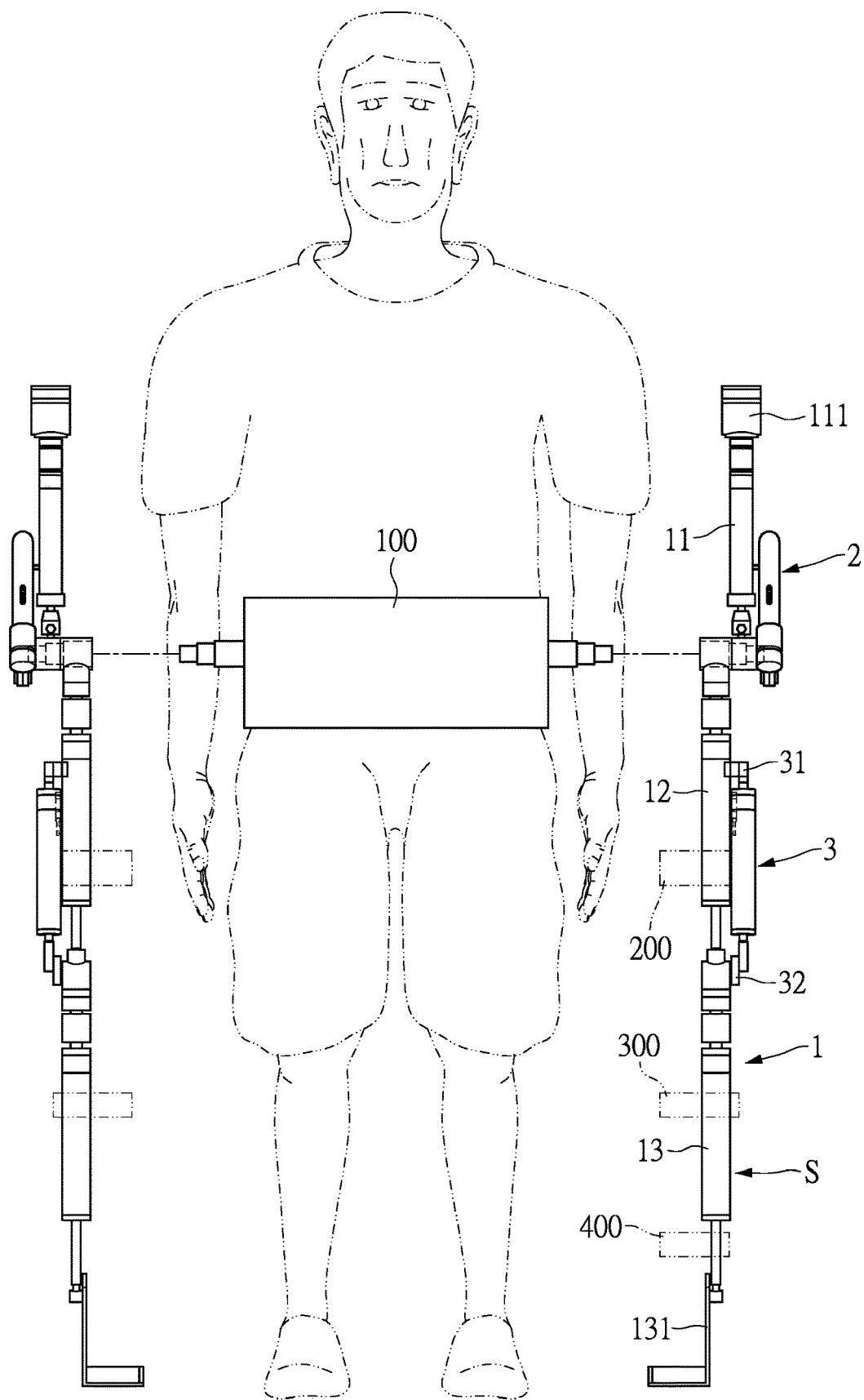
FIG. 10 is another schematic view of the assistant apparatus for degenerative joint of the present disclosure in operation.

The upper section 11 of the apparatus main body 1 is provided with a supporting member 111. The supporting member 111 can be placed under the armpit of the user so that the apparatus main body 1 can function like a crutch to support the weight of the human body. The lower end of lower section 13 is provided with a carrying member 131, which can be placed inside the user's shoe to uphold the user's foot. In addition, the apparatus main body 1 can also use fastening members 100, 200, 300 and 400 (as shown in FIG. 10) such as Velcro tapes or webbing to be fixed onto the user's body, thighs and calves, so that apparatus main body 1 can be as close to the human body as possible. The apparatus main body 1 may also include a handgrip 14, which may be connected to the middle section 12 for the user to hold.

The upper section 11, the middle section 12, the lower section 13, the first leg-lifting mechanism 2, and the second leg-lifting mechanism 3 of the apparatus main body 1 each include an elastic buffering mechanism S. That is, all above-mentioned devices have elastic members to provide elastic buffering effects. The upper section 11, the middle section 12, and the lower section 13 of the apparatus main body 1 each include the elastic buffering mechanism, which provides the apparatus main body 1 with elasticity. The first leg-lifting mechanism 2 is connected between the upper section 11 and middle section 12 of the apparatus main body 1. The second leg-lifting mechanism 3 is connected between the middle section 12 and the lower section 13 of the apparatus main body 1. The first leg-lifting mechanism 2 and the second leg-lifting mechanism 3 both have the elastic buffering mechanism S, so that the first leg-lifting mechanism 2 can be used to assist the user to lift his thigh, and the second leg-lifting mechanism 3 can be used to assist the user to lift his calf.

Here, the structures of these elastic buffering mechanisms S are not limited. For example, the structures of these elastic buffering mechanisms S may be the same or different. In this embodiment, the structures of these elastic buffering mechanisms S are substantially the same. Therefore, for the sake of brevity, only the structure of the elastic buffering mechanism S of the upper section 11 of the apparatus main body 1 is specifically described herein. As shown in FIG. 4 to FIG. 8, the elastic buffering mechanism S includes a tube body S1, an adjusting member S2, a bolt S3, a nut S4, a first elastic member S5, a second elastic member S6, a sliding assembly S7, and a connecting rod S8.

The tube body S1 is a hollow object that can either be straight or curved, and there is no limitation to its shape. In this embodiment, the tube bodies S1 of the elastic buffering mechanisms S of the upper section 11, the middle section 12, the lower section 13, and the second leg-lifting mechanism 3 of the apparatus main body 1 are all straight. The tube body S1 of the elastic buffering mechanism S of the first leg-lifting mechanism 2 is curved.

The adjusting member S2 is disposed at the upper end of the tube body S1, and the bolt S3 is disposed inside the tube body S1. The adjusting member S2 is fixed at one end of the bolt S3, so that the adjusting member S2 can be used to drive the bolt S3 to rotate. The nut S4 is disposed inside the tube body S1 and screwed to the bolt S3. The nut S4 can include a guiding member S41. The guiding member S41 is slidably fitted in a guiding groove S11 of the tube body S1 and extends along the axial direction of the tube body S1 to guide the movement of the nut S4.

The first elastic member S5, the second elastic member S6, the sliding assembly S7, and the connecting rod S8 are disposed inside the tube body S1. The first elastic member S5 and the second elastic member S6 can both be elastic members such as compression springs. The diameter of first elastic member S5 is larger than that of the second elastic member S6. The sliding assembly S7 is disposed between the first elastic member S5 and the second elastic member S6. The upper end of the connecting rod S8 is connected to the sliding assembly S7. The lower end of the connecting rod S8 extends out of the tube body S1 such that the connecting rod S8 can be connected to the adjacent devices such as the upper end of the middle section 12. The sliding assembly S7 can include one slider S71 and two magnets S72 and S73, and the two magnets S72 and S73 are disposed above the slider S71. The slider S71 and the two magnets S72 and S73 are movably disposed in the tube body S1. The adjacent sides of the magnets S72 and S73 have the same magnetic polarity, so that the magnets S72 and S73 can generate repulsive force, so as to increase the upward pushing force against the first elastic member S5 and the second elastic member S6. The upper end of the connecting rod S8 is connected to the slider S71 of sliding assembly S7.

When the adjusting member S2 is driving the bolt S3 to rotate, the nut S4 is pushed to move inside the tube body S1 along the axial direction thereof. This drives the nut S4 to push upward against the first elastic member S5, the sliding assembly S7, and the second elastic member S6, thereby changing the lengths of the first elastic member S5 and the second elastic member S6. When the first elastic member S5 and the second elastic member S6 become shorter, their elasticities are reduced. When the first elastic member S5 and the second elastic member S6 become longer, their elasticities increase. In this manner, the elastic buffering mechanism S can have an adjustment function of different elasticity and tightness.

Specifically, the adjusting member S2 and the connecting rod S8 of the elastic buffering mechanism S can be used to connect the upper section 11, the middle section 12, and the lower section 13 of the apparatus main body 1. For example, the adjusting member S2 of the elastic buffering mechanism S of the middle section 12 can be connected to the connecting rod S8 of the elastic buffering mechanism S of the upper section 11 through a first connecting assembly 121. The connecting rod S8 of the elastic buffering mechanism S of the middle section 12 can be connected to the adjusting member S2 of the elastic buffering mechanism S of the lower section 13 through a second connecting assembly 132. The first connecting assembly 121 and the second connecting assembly 132 may include existing connecting members such as rotating shafts and connecting rods, but are not limited thereto.

The tube body S1 and the connecting rod S8 of the elastic buffering mechanism S can be used to connect the upper section 11, the middle section 12, and the first leg-lifting mechanism 2 of the apparatus main body 1. For example, the tube body S1 of the elastic buffering mechanism S of the first leg-lifting mechanism 2 can be connected to the tube body S1 of the elastic buffering mechanism S of the upper section 11 through a third connecting assembly 21. The connecting rod S8 of the elastic buffering mechanism S of the first leg-lifting mechanism 2 can be connected to the upper end of middle section 12 through a fourth connecting assembly 22. The third connecting assembly 21 and the fourth connecting assembly 22 may include existing connecting members such as rotating shafts and connecting rods, but are not limited thereto.

The adjusting member S2 and the connecting rod S8 of the elastic buffering mechanism S can be used to connect the middle section 12, the lower section 13, and the second leg-lifting mechanism 3 of the apparatus main body 1. For example, the adjusting member S2 of the elastic buffering mechanism S of the second leg-lifting mechanism 3 can be connected to the tube body S1 of the elastic buffering mechanism S of the middle section 12 through a fifth connecting assembly 31. The connecting rod S8 of the elastic buffering mechanism S of the second leg-lifting mechanism 3 can be connected to the upper end of the lower section 13 through a sixth connecting assembly 32. The fifth connecting assembly 31 and the sixth connecting assembly 32 may include existing connecting members such as rotating shafts and connecting rods, but are not limited thereto.

Figure 9:
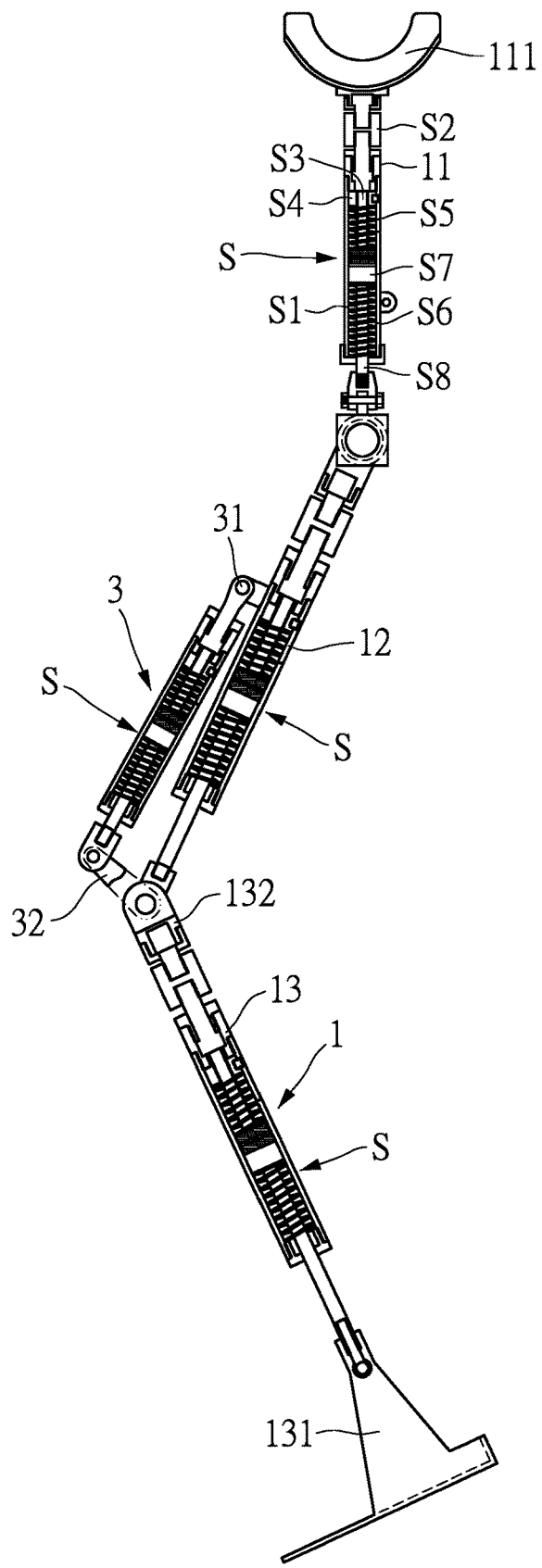
FIG. 9 is a schematic view of the assistant apparatus for degenerative joint of the present disclosure in operation.

As shown in FIG. 9 and FIG. 10, the assistant apparatus for degenerative joint in accordance with the present disclosure includes the apparatus main body 1, the first leg-lifting mechanism 2, and the second leg-lifting mechanism 3. The assistant apparatus can be worn onto the human body to assist with walking. The apparatus main body 1 has the upper section 11, the middle section 12, and the lower section 13. The assistant apparatus can support the weight of the human body in a multi-sectional manner and can provide an elastic buffering effect using the elastic buffering mechanism S of each section. The assistant apparatus can also store kinetic energy through body weight when stepped down on, and coupled with the designs of the first leg-lifting mechanism 2 and the second leg-lifting mechanism 3, can assist users to lift their thighs and calves.

In conclusion, the assistant apparatus of the present disclosure is a kind of walking crutch that can support the weight of the human body in a multi-sectional manner and generate an elastic buffering effect. It can also use the weight of the human body to store kinetic energy when it is stepped down on, so that users can save energy when they lift their thighs and calves. The assistant apparatus of the present disclosure can effectively reduce the discomfort of the waist and the joints, and is suitable for patients with symptoms such as deteriorative joints, osteoporosis, mild stroke, as well as for traffic accident rehabilitation so that patients can walk more effortlessly and easily. Furthermore, the elastic buffering mechanism of the assistant apparatus of the present disclosure has an adjustment function, with which the elastic force can be appropriately adjusted according to the heights of the users and the use conditions.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. An assistant apparatus for degenerative joint, comprising:

an apparatus main body including an upper section, a middle section, and a lower section, wherein the middle section is connected between the upper section and the lower section, an upper end of the upper section is provided with a supporting member, a lower end of the lower section is provided with a carrying member, the upper section is bendable relative to the middle section, and the middle section is bendable relative to the lower section;

a first leg-lifting mechanism connected between the upper section and the middle section of the apparatus main body; and a second leg-lifting mechanism connected between the middle section and the lower section of the apparatus main body;

wherein the upper section, the middle section, the lower section, the first leg-lifting mechanism, and the second leg-lifting mechanism of the apparatus main body each includes an elastic buffering mechanism for providing elastic buffering effects, wherein the elastic buffering mechanism includes a tube body, an adjusting member, a bolt, a nut, a first elastic member, a second elastic member, a sliding assembly, and a connecting rod, wherein the adjusting meme is disposed at an upper end of the tube body, the bolt is disposed inside the tube body, the adjusting member is fixed at one end of the bolt, and the nut is disposed inside the tube body and screwed to the bolt, wherein the first elastic member, the second elastic member, the sliding assembly and the connecting rod are disposed inside the tube body, and the sliding assembly is disposed between the first elastic member and the second elastic member, wherein an upper end of the connecting rod is connected to the sliding assembly, and a lower end of the connecting rod extends out of the tube body, and wherein, when the adjusting member is driving the bolt to rotate, the bolt pushes the nut to move inside the rube body along an axial direction of the tube body to drive the nut to push the first elastic member, the sliding assembly, and the second elastic member such that the elastic buffering mechanism is adjustable.

2. The assistant apparatus for degenerative joint according to claim 1, wherein the adjusting member of the elastic buffering mechanism of the middle section is connected to the connecting rod of the elastic buffering mechanism of the upper section through a first connecting assembly, and the connecting rod of the elastic buffering mechanism of the middle section is connected to the adjusting member of the elastic buffering mechanism of the lower section through a second connecting assembly.

3. The assistant apparatus for degenerative joint according to claim 1, wherein the tube bodies of the elastic buffering mechanisms of the upper section, the middle section, the lower section, and the second leg-lifting mechanism are all straight, and the tube body of the elastic buffering mechanism of the first leg-lifting mechanism is curved.

* * * * *